(12) United States Patent
Keshwani

(10) Patent No.: US 12,314,345 B2
(45) Date of Patent: May 27, 2025

(54) LEARNING APPARATUS, LEARNING METHOD, AND LEARNING PROGRAM, CLASS CLASSIFICATION APPARATUS, CLASS CLASSIFICATION METHOD, AND CLASS CLASSIFICATION PROGRAM, AND LEARNED MODEL

(71) Applicant: FUJIFILM Corporation, Tokyo (JP)

(72) Inventor: Deepak Keshwani, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 407 days.

(21) Appl. No.: 17/556,983

(22) Filed: Dec. 20, 2021

(65) Prior Publication Data

US 2022/0114393 A1    Apr. 14, 2022

Related U.S. Application Data

(63) Continuation of application No. PCT/JP2020/025400, filed on Jun. 26, 2020.

(30) Foreign Application Priority Data

Jun. 27, 2019   (JP) .................................. 2019-119982

(51) Int. Cl.
*G16H 30/40* (2018.01)
*A61B 6/00* (2024.01)
(Continued)

(52) U.S. Cl.
CPC ...... *G06F 18/2148* (2023.01); *G06F 18/2431* (2023.01); *G06N 3/045* (2023.01);
(Continued)

(58) Field of Classification Search
None
See application file for complete search history.

(56) References Cited

U.S. PATENT DOCUMENTS

| | | | |
|---|---|---|---|
| 2016/0089074 A1 | 3/2016 | Wang | |
| 2018/0374209 A1* | 12/2018 | Patil | ........................ G06N 3/084 |
| 2019/0034762 A1 | 1/2019 | Hashimoto | |

FOREIGN PATENT DOCUMENTS

| | | |
|---|---|---|
| JP | 2016067610 | 5/2016 |
| JP | 2019028616 | 2/2019 |

OTHER PUBLICATIONS

Korshunova, Kseniya P. "A Convolutional Fuzzy Neural Network for Image Classification." 2018 3rd Russian-Pacific Conference on Computer Technology and Applications (RPC), 2018, pp. 1-4. IEEE Xplore, https://doi.org/10.1109/RPC.2018.8482211. (Year: 2018).*

(Continued)

*Primary Examiner* — Matthew C Bella
*Assistant Examiner* — Johnny B Duong
(74) *Attorney, Agent, or Firm* — JCIPRNET

(57) ABSTRACT

A first learning unit performs learning of a first neural network that extracts a feature vector in each pixel of a target image including a plurality of objects and that outputs a feature map in which feature vectors of pixels belonging to individual objects included in the target image are clustered and distributed as a plurality of the feature vector groups in a feature space which is a space of the feature vector. A second learning unit performs learning of a second neural network that outputs a class classification result of a plurality of objects belonging to the same category included in the target image in response to input of the feature vector of the target image.

15 Claims, 8 Drawing Sheets

(51) Int. Cl.
  *G01T 1/29* (2006.01)
  *G06F 18/214* (2023.01)
  *G06F 18/2431* (2023.01)
  *G06N 3/045* (2023.01)
  *G06V 10/764* (2022.01)
  *G06V 10/82* (2022.01)
  *G16H 50/20* (2018.01)

(52) U.S. Cl.
  CPC ............ *G06V 10/764* (2022.01); *G06V 10/82* (2022.01); *G16H 30/40* (2018.01); *G16H 50/20* (2018.01); *A61B 6/5205* (2013.01); *G01T 1/2985* (2013.01); *G06V 2201/03* (2022.01)

(56) References Cited

OTHER PUBLICATIONS

Liu, Pin-Hsien, et al. "Two Staged Machine Learning Network for Spine Segmentation and Recognition." 2018 IEEE International Symposium on Multimedia (ISM), 2018, pp. 194-197. IEEE Xplore, https://doi.org/10.1109/ISM.2018.000-8. (Year: 2018).*

Ma, Xiao, et al. Fully Convolutional Network with Cluster for Semantic Segmentation. 2018, p. 040049. DOI.org (Crossref), https://doi.org/10.1063/1.5033713. (Year: 2018).*

Morrison, Doug, Anton Milan, and Nontas Antonakos. "Estimating uncertainty in instance segmentation using dropout sampling." (2019). (Year: 2019).*

Wu, Zifeng, et al. Wider or Deeper: Revisiting the ResNet Model for Visual Recognition. 2016. DOI.org (Datacite), https://doi.org/10.48550/ARXIV.1611.10080. (Year: 2016).*

Lavdas, Ioannis, et al. "Fully automatic, multiorgan segmentation in normal whole body magnetic resonance imaging (MRI), using classification forests (CF s), convolutional neural networks (CNN s), and a multi-atlas (MA) approach." Medical physics 44.10 (2017): 5210-5220. (Year: 2017).*

Lessmann, Nikolas, et al. "Iterative fully convolutional neural networks for automatic vertebra segmentation and identification." Medical image analysis 53 (2019): 142-155. https://arxiv.org/abs/1804.04383. (Year: 2019).*

"Office Action of Japan Counterpart Application", issued on Feb. 28, 2023, with English translation thereof, p. 1-p. 5.

Bert De Brabandere et al., "Semantic Instance Segmentation with a Discriminative Loss Function," Deep Learning for Robotic Vision, workshop at CVPR 2017, Aug. 2017, pp. 1-10.

Alireza Fathi et al., "Semantic Instance Segmentation via Deep Metric Learning," Computer Vision and Pattern Recognition, Mar. 2017, pp. 1-9.

Shu Kong et al., "Recurrent Pixel Embedding for Instance Grouping," Computer Vision and Pattern Recognition (cs.CV); Machine Learning (cs.LG); Multimedia (cs.MM), Dec. 2017, pp. 1-24.

"International Search Report (Form PCT/ISA/210) of PCT/JP2020/025400," mailed on Aug. 25, 2020, with English translation thereof, pp. 1-4.

"Written Opinion of the International Searching Authority (Form PCT/ISA/237)" of PCT/JP2020/025400, mailed on Aug. 25, 2020, with English translation thereof, pp. 1-8.

* cited by examiner

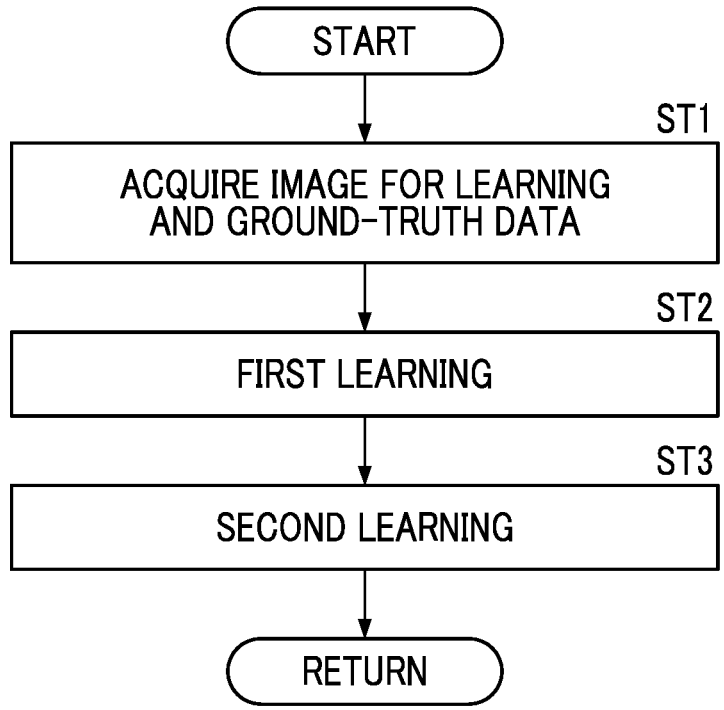
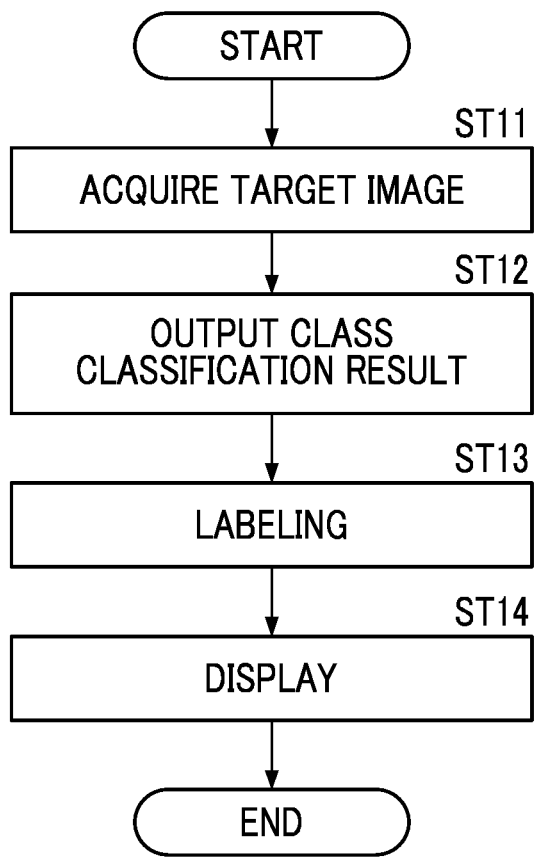

LEARNING APPARATUS, LEARNING METHOD, AND LEARNING PROGRAM, CLASS CLASSIFICATION APPARATUS, CLASS CLASSIFICATION METHOD, AND CLASS CLASSIFICATION PROGRAM, AND LEARNED MODEL

CROSS REFERENCE TO RELATED APPLICATIONS

The present application is a Continuation of PCT International Application No. PCT/JP2020/025400, filed on Jun. 26, 2020, which claims priority to Japanese Patent Application No. 2019-119982, filed on Jun. 27, 2019. Each application above is hereby expressly incorporated by reference, in its entirety, into the present application.

BACKGROUND

Technical Field

The present disclosure relates to a learning apparatus, a learning method, and a learning program, which perform learning of neural networks that discriminate objects included in an image, a class classification apparatus, a class classification method, and a class classification program, which classify classes of the objects included in the image, and a learned model.

Related Art

In recent years, machine learning techniques using deep learning have been attracting attention. In particular, various techniques have been proposed in the field of class classification for discriminating objects included in an image. For example, semantic segmentation is well-known in which class classification is performed by labeling all pixels of an image on a pixel-by-pixel basis. However, since semantic segmentation performs segmentation without distinguishing individual objects of the same category, it is not possible to distinguish individual objects in a case where objects of the same category overlap. Therefore, an instance segmentation method of distinguishing and segmenting individual objects has been proposed (see, for example, Semantic Instance Segmentation with a Discriminative Loss Function, Bert De Brabandere, Davy Neven, Luc Van Gool, Computer Vision and Pattern Recognition, "Deep Learning for Robotic Vision", workshop at CVPR 2017, Submitted on 8 Aug. 2017, Semantic Instance Segmentation via Deep Metric Learning, Alireza Fathi, Zbigniew Wojna, Vivek Rathod, Peng Wang, Hyun Oh Song, Sergio Guadarrama, Kevin P. Murphy, Computer Vision and Pattern Recognition, Submitted on 30 Mar. 2017, and Recurrent Pixel Embedding for Instance Grouping, Shu Kong, Charless Fowlkes, Computer Vision and Pattern Recognition (cs.CV); Machine Learning (cs.LG); Multimedia (cs.MM), Submitted on 22 Dec. 2017). In a case where the instance segmentation is used, individual objects can be distinguished and segmented even in a case where the objects are in the same category. Therefore, the objects can be individually segmented even in a case where the objects of the same category overlap.

With the above-mentioned instance segmentation method, the individual objects of the same category can be distinguished and segmented. Meanwhile, a plurality of objects of the same category included in the image may be classified into a plurality of classes. For example, a plurality of vertebrae constituting the human vertebral column can be classified into three classes of the cervical vertebrae, the thoracic vertebrae, and the lumbar vertebrae. However, the instance segmentation method can distinguish and segment the individual vertebrae included in the image, but cannot classify the segmented vertebrae into individual classes, such as the cervical vertebrae, the thoracic vertebrae, and the lumbar vertebrae.

SUMMARY OF THE INVENTION

The present disclosure has been made in view of the above circumstances, and an object thereof is to make it possible to further perform class classification of a plurality of objects belonging to the same category included in an image.

A learning apparatus according to the present disclosure, comprises: a first learning unit that causes a first neural network which extracts a feature vector in each pixel of a target image including a plurality of objects and which outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and that derives a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and a second learning unit that causes a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of the feature vectors for the objects belonging to the same category, and that derives a second loss for the class classification result on the basis of the class classification result for learning and the ground-truth data, to perform learning of the second neural network on the basis of the second loss.

In the learning apparatus according to the present disclosure, the representative value of the feature vectors may be a representative value of feature vectors included in a feature vector group that corresponds to each of the individual objects belonging to the same category included in the image for learning.

Alternatively, in the learning apparatus according to the present disclosure, the representative value of the feature vectors may be a representative value of feature vectors of all the objects belonging to the same category included in the image for learning.

Further, in the learning apparatus according to the present disclosure, the representative value may be at least one of an average value, a weighted average value, a median value, a minimum value, or a maximum value of the feature vectors.

Further, in the learning apparatus according to the present disclosure, the first neural network may be a fully convolutional neural network.

Further, in the learning apparatus according to the present disclosure, the second neural network may be a fully connected neural network.

Further, in the learning apparatus according to the present disclosure, the target image and the image for learning may be three-dimensional medical images.

Further, in the learning apparatus according to the present disclosure, the object may be a vertebra, and the class classification result may be a classification result of the vertebrae into at least one of cervical vertebrae, thoracic vertebrae, or lumbar vertebrae.

A class classification apparatus according to the present disclosure, comprises a class classification unit to which a learned model including the first neural network and the second neural network of which learning is performed by the learning apparatus according to the present disclosure is applied, and which outputs a class classification result of a plurality of objects belonging to the same category included in the target image in response to input of the target image.

In the class classification apparatus according to the present disclosure, a labeling unit that labels the objects included in the target image according to the class classification result, and a display control unit that displays the labeled target image on a display unit may further be provided.

A learned model according to the present disclosure, comprises the first neural network and the second neural network of which learning is performed by the learning apparatus according to the present disclosure.

A learning method according to the present disclosure, comprises: causing a first neural network which extracts a feature vector in each pixel of a target image including a plurality of objects and outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and deriving a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and causing a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of feature vectors for the objects belonging to the same category, and deriving a second loss for the class classification result on the basis of the class classification result for learning and the ground-truth data, to perform learning of the second neural network on the basis of the second loss.

A class classification method according to the present disclosure, comprises outputting a class classification result of a plurality of objects belonging to the same category included in the target image in response to input of the target image, by using a learned model including the first neural network and the second neural network of which learning is performed by the learning method according to the present disclosure.

The learning method and the class classification method according to the present disclosure may be provided as programs to be executed by a computer.

Another learning apparatus according to the present disclosure, comprises: a memory that stores a command to be executed by a computer; and a processor configured to execute the stored command, in which the processor executes a process including causing a first neural network which extracts a feature vector in each pixel of a target image including a plurality of objects and outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and deriving a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and causing a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of feature vectors for the objects belonging to the same category, and deriving a second loss for the class classification result on the basis of the class classification result for learning and the ground-truth data, to perform learning of the second neural network on the basis of the second loss.

Another class classification apparatus according to the present disclosure, comprises: a memory that stores a command to be executed by a computer; and a processor configured to execute the stored command, in which the processor executes a process including outputting a class classification result of a plurality of objects belonging to the same category included in the target image in response to input of the target image, by using a learned model including the first neural network and the second neural network of which learning is performed by the learning apparatus according to the present disclosure.

According to the present disclosure, the class classification of a plurality of objects belonging to the same category included in the target image can be further performed.

BRIEF DESCRIPTION OF THE DRAWINGS

FIG. 9 is a flowchart showing learning processing performed in the present embodiment.

FIG. 10 is a flowchart showing class classification processing performed in the present embodiment.

DETAILED DESCRIPTION

Figure 1:
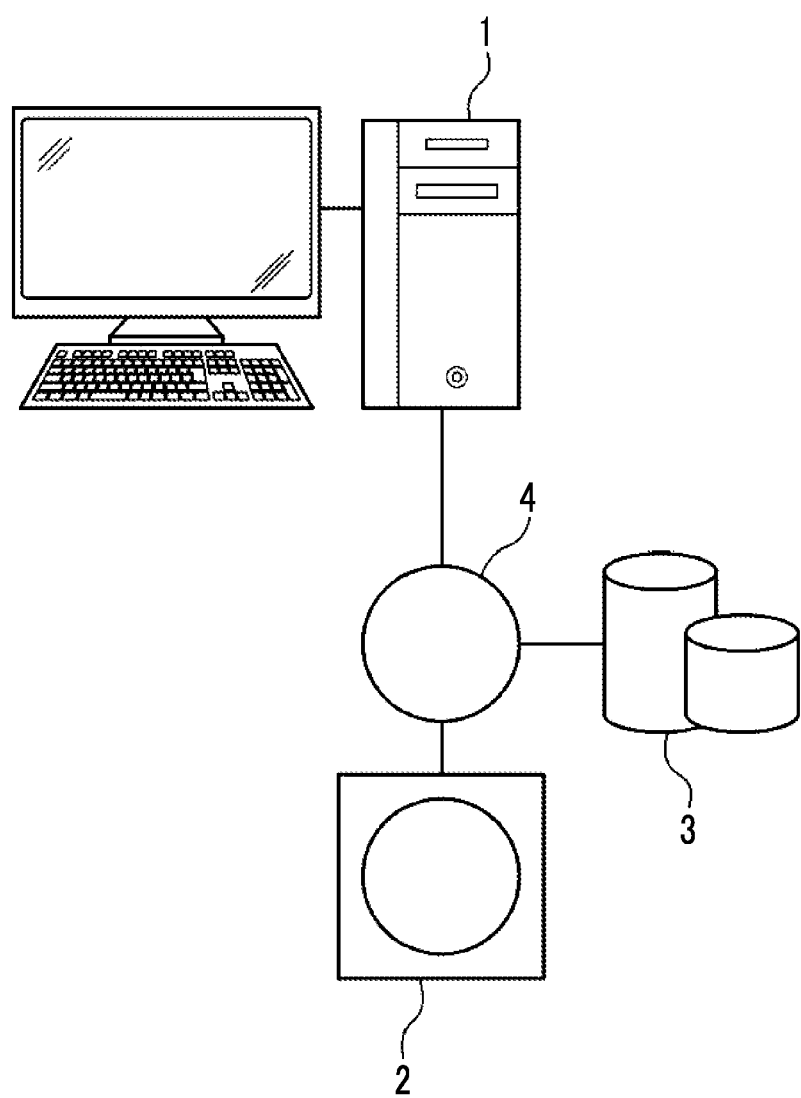
FIG. 1 is a hardware configuration diagram showing an outline of a diagnosis support system to which a learning apparatus and a class classification apparatus according to an embodiment of the present disclosure are applied.

Hereinafter, an embodiment of the present disclosure will be described with reference to the drawings. FIG. 1 is a hardware configuration diagram showing an outline of a diagnosis support system to which a learning apparatus and a class classification apparatus according to the embodiment of the present disclosure are applied. As shown in FIG. 1, in the diagnosis support system, a learning apparatus and class classification apparatus 1 (hereinafter, simply referred to as a class classification apparatus), a three-dimensional image capturing apparatus 2, and an image storage server 3 according to the present embodiment are connected to communicate with one another via a network 4.

The three-dimensional image capturing apparatus 2 is an apparatus that images an area to be diagnosed of a subject and that generates a three-dimensional image representing the area, and specific examples thereof include a CT apparatus, an MRI apparatus, and a positron emission tomography (PET) apparatus. The three-dimensional image generated by the three-dimensional image capturing apparatus 2 is transmitted to and stored in the image storage server 3. In the present embodiment, the three-dimensional image capturing apparatus 2 is a CT apparatus and generates a CT image including the area to be diagnosed of the subject, as a three-dimensional image. In addition, the three-dimensional image consists of a plurality of tomographic images. Further, in the present embodiment, a plurality of vertebrae constituting the vertebral column included in the three-dimensional image are a class classification target.

The image storage server 3 is a computer that stores and manages various data and comprises a large-capacity external storage device and database management software. The image storage server 3 communicates with another apparatus via a wired or wireless network 4 to transmit and receive image data and the like. Specifically, the image storage server 3 acquires various data including the image data of the three-dimensional image generated by the three-dimensional image capturing apparatus 2 via the network, and stores and manages the acquired data on a recording medium such as a large-capacity external storage device. A storage format of the image data and the communication between the apparatuses via the network 4 are based on a protocol such as digital imaging and communications in medicine (DICOM). Further, in the present embodiment, the image storage server 3 also stores and manages an image for learning that is used to perform learning of a neural network, which will be described later.

The class classification apparatus 1 including the learning apparatus of the present embodiment is an apparatus obtained by installing a learning program and a class classification program of the present embodiment on one computer. The computer may be a workstation or a personal computer directly operated by a doctor who makes diagnosis, or may be a server computer connected to the workstation or the personal computer via a network. The learning program and the class classification program are stored on a storage device of a server computer connected to the network or on network storage so as to be accessible from the outside, and are downloaded and installed on a computer that the doctor uses according to a request. Alternatively, the learning program and the class classification program are recorded on a recording medium, such as a digital versatile disc (DVD) or a compact disc read only memory (CD-ROM), and are distributed and installed on a computer from the recording medium.

Figure 2:
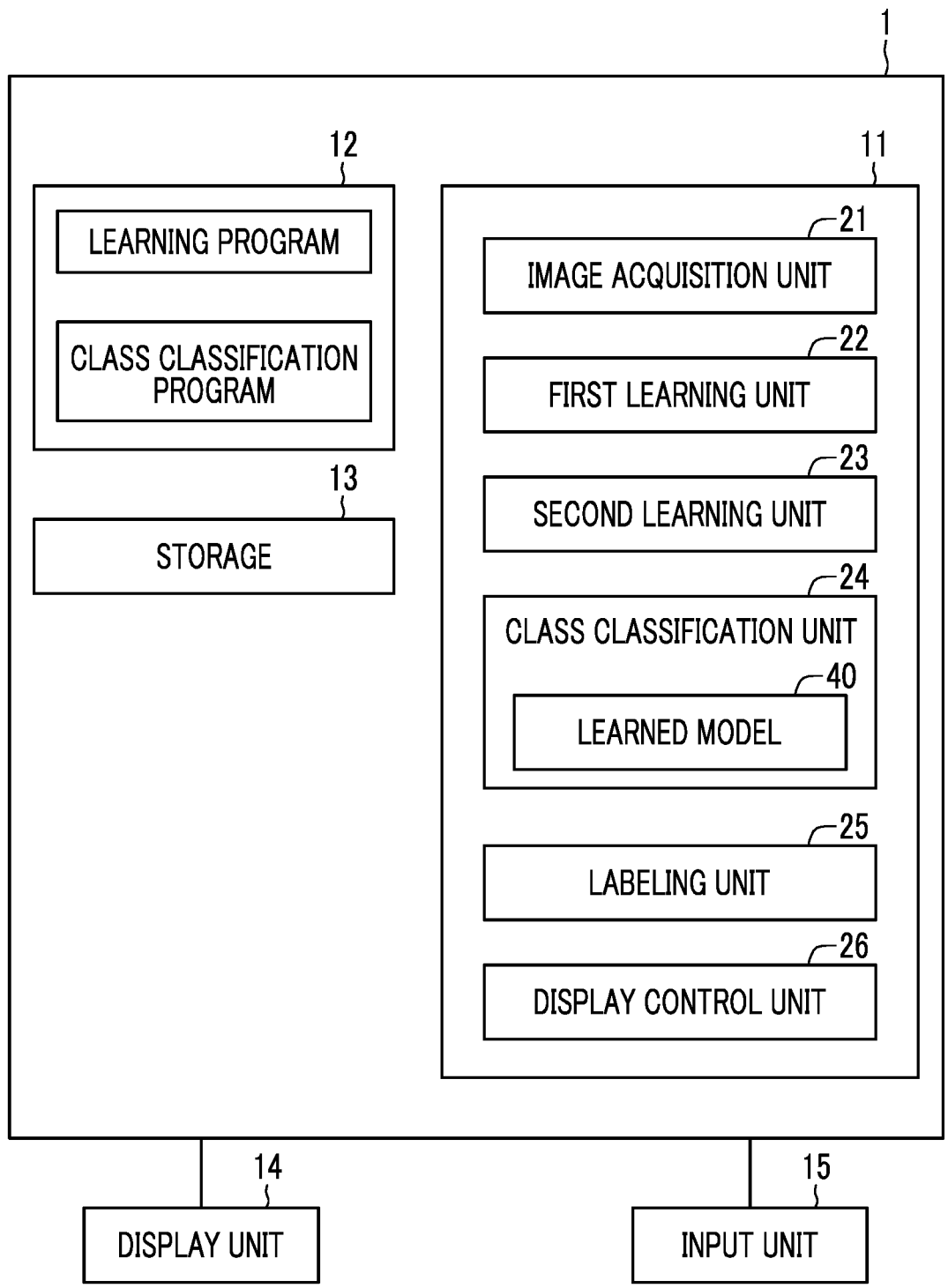
FIG. 2 is a diagram showing a schematic configuration of the class classification apparatus according to the embodiment of the present disclosure.

FIG. 2 is a diagram showing the schematic configuration of the class classification apparatus which is realized with the learning program and the class classification program installed on a computer. As shown in FIG. 2, the class classification apparatus 1 comprises a central processing unit (CPU) 11, a memory 12, and a storage 13, as a standard workstation configuration. Further, a display unit 14, such as a liquid crystal display, and an input unit 15, such as a keyboard and a mouse, are connected to the class classification apparatus 1.

The storage 13 includes a hard disk drive or the like, and stores a target image, as a class classification target, acquired from the image storage server 3 via the network 4, an image for learning that is used to perform learning of the neural network, which will be described later, and various information including information required for processing.

Further, the learning program and the class classification program are stored in the memory 12. The learning program defines, as processing to be executed by the CPU 11, image acquisition processing of acquiring an image for learning that is used to perform learning of a first neural network and a second neural network, which will be described later, and a target image as a class classification target, first learning processing of deriving a first loss that is used to perform learning of the first neural network on the basis of the first loss, and second learning processing of deriving a second loss that is used to perform learning of the second neural network, which will be described later, to perform learning of the second neural network on the basis of the second loss.

The class classification program defines, as processing to be executed by the CPU 11, class classification processing of outputting a class classification result of a plurality of objects belonging to the same category included in the target image, as a class classification target, acquired by the image acquisition processing, labeling processing of labeling the objects included in the target image according to the class classification result, and display control processing of displaying the labeled target image on the display unit 14.

The CPU 11 executes the processing according to the learning program and the class classification program, so that the computer functions as an image acquisition unit 21, a first learning unit 22, a second learning unit 23, a class classification unit 24, a labeling unit 25, and a display control unit 26.

The image acquisition unit 21 acquires, as the target image, the three-dimensional image including the vertebrae, from the image storage server 3 via an interface (not shown) connected to the network. The image acquisition unit 21 also acquires an image for learning that is used to perform learning and ground-truth data, which will be described later.

The first learning unit 22 performs learning of a first neural network N1 that extracts a feature vector in each pixel of a target image including a plurality of objects (in the present embodiment, vertebrae) and that outputs a feature map in which feature vectors of pixels belonging to individual objects included in the target image are clustered and distributed as a plurality of feature vector groups in a feature space which is a space of the feature vector. Specifically, the first learning unit 22 performs learning of the first neural network N1 so that the first neural network N1 outputs the feature map in which the feature vectors for individual objects included in the target image are clustered and distributed as clusters consisting of a plurality of feature vector groups, in the feature space.

The second learning unit 23 performs learning of a second neural network N2 that outputs a class classification result of which class of a plurality of classes the plurality of objects belonging to the same category included in the target image belong to, in response to the input of the feature vector of the target image. Specifically, the second learning unit 23 performs learning of the second neural network N2 so that the second neural network N2 outputs the probabilities that the clusters corresponding to individual objects included in the feature map belong to the plurality of classes, respectively, in response to the input of the feature vector of the target image.

Figure 3:
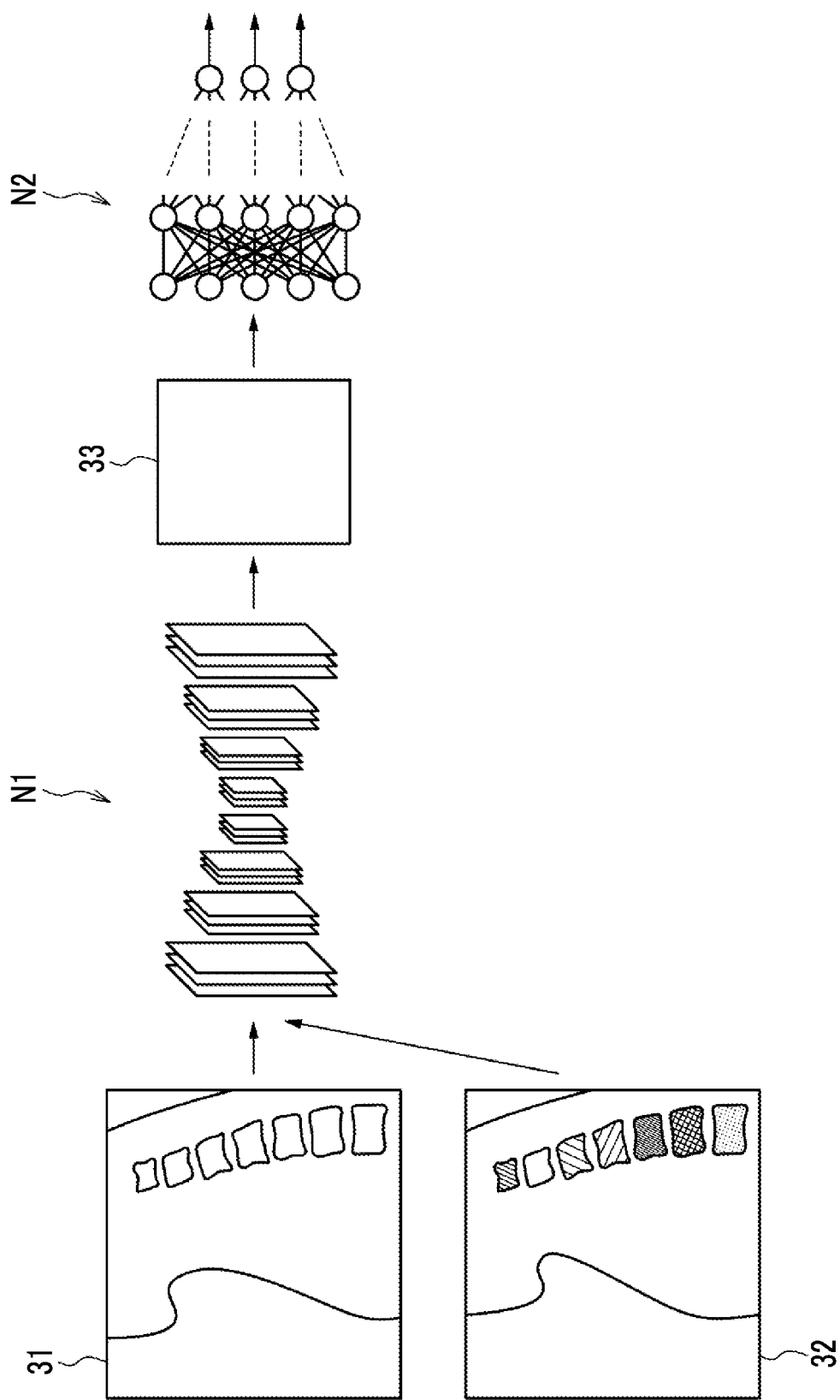
FIG. 3 is a schematic block diagram for explaining configurations and learning processing of a first neural network and a second neural network.

FIG. 3 is a schematic block diagram for explaining the configurations and learning processing of the first neural network N1 and the second neural network N2. As shown in FIG. 3, the first learning unit 22 causes the first neural network N1 to output the feature map for learning 33 in response to the input of an image for learning 31 and ground-truth data 32. The feature map for learning 33 is formed by clustering and distributing the feature vectors of each voxel in the image for learning 31 for each individual object included in the image for learning 31.

Here, the image for learning 31 includes all or a part of the vertebrae constituting the human vertebral column. Further, the ground-truth data 32 is data in which the individual vertebrae included in the image for learning 31 are distinguished. In addition, in FIG. 3, it is shown that individual vertebrae are distinguished with different hatching patterns. Further, the ground-truth data 32 also includes information on the result of which class of the cervical vertebrae, the thoracic vertebrae, or the lumbar vertebrae each vertebra is classified into.

The first neural network N1 consists of a convolutional neural network (hereinafter, referred to as a CNN), which is one of multi-layer neural networks in which a plurality of processing layers are hierarchically connected. Further, since all the input layers of the processing layer of the first neural network N1 consist of convolutional layers, the first neural network N1 is a fully convolutional neural network. The convolutional layer performs convolution processing using various kernels on the input image, and outputs a feature map consisting of feature data obtained by the convolution processing. The kernel has an n×n pixel size (for example, n=3), and each element is weighted. Specifically, weight such as a differential filter that emphasizes the edge of the input image is set. The convolutional layer applies the kernel to the entire input image or feature map output from the previous processing layer, while shifting the pixel of interest of the kernel. Furthermore, the convolutional layer applies an activation function such as a sigmoid function to the convolution value, and outputs a feature map.

In the present embodiment, the first learning unit 22 causes the first neural network N1 to output the feature map for learning 33 for the image for learning 31 in a case where the image for learning 31 and the ground-truth data 32 for the class classification result regarding the plurality of objects belonging to the same category included in the image for learning 31 are input to the first neural network N1. In the present embodiment, the first neural network N1 generates the feature map for learning 33 such that the distance in feature vector between pixels belonging to the same object included in the image for learning 31 becomes small and the distance in feature vector between pixels belonging to the different objects becomes large. Therefore, the first learning unit 22 derives a first loss Linst between pixels in the image for learning 31 as a function in which the distance in feature vector between pixels belonging to the same object in the image for learning 31 becomes small, and the distance in feature vector between pixels belonging to the different objects becomes large, on the basis of the distribution of the plurality of feature vector groups in the feature map for learning 33 and the ground-truth data 32.

Figure 4:
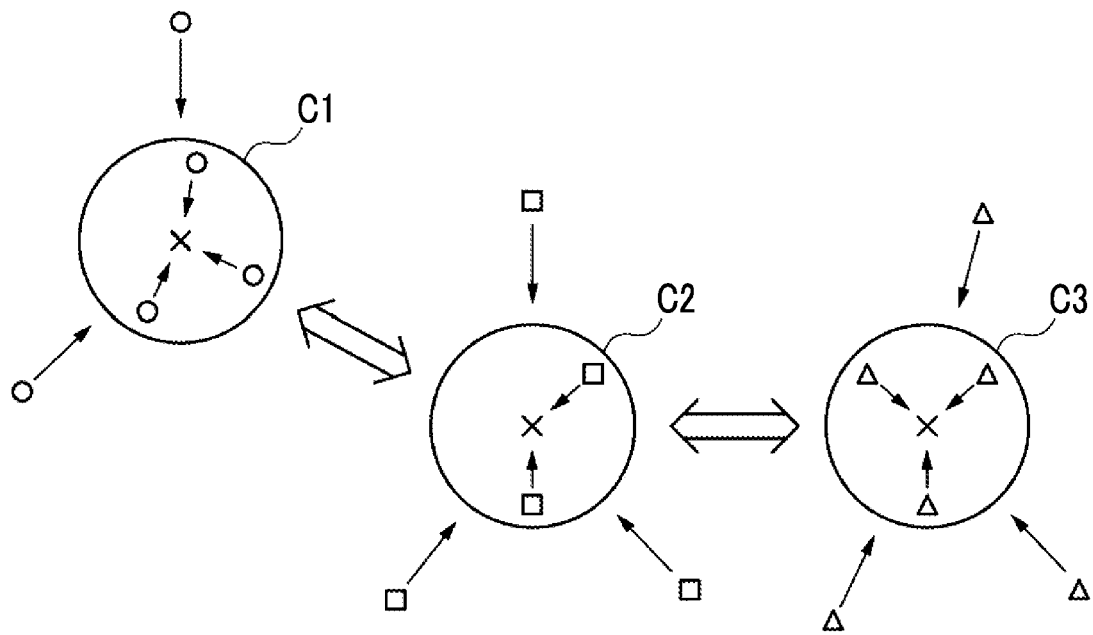
FIG. 4 is a conceptual diagram of generation of a feature map.

FIG. 4 is a conceptual diagram of the generation of the feature map. FIG. 4 shows the feature vectors for each of the three objects by circles, squares, and triangles. Feature vectors represented by the same shape correspond to the same object. As shown in FIG. 4, a feature map is generated such that the feature vectors of the same object become close to each other as shown by the single-headed arrow and the feature vectors of different objects become far away from each other as shown by the double-headed arrow. As a result, the feature vectors are clustered and distributed as the three clusters C1 to C3 shown by the circles in FIG. 4 in the feature space. In the present embodiment, the three clusters C1 to C3 in the feature space are standardized so as to be distributed within a predetermined range in the feature space.

A function in which the distance in feature vector between pixels belonging to the same object in the image for learning 31 becomes small is represented by Equation (1). In addition, a function in which the distance in feature vector between pixels belonging to the different objects becomes large is represented by Equation (2). Further, a function for standardization is represented by Equation (3). The function (1) represents the loss Lvar based on the feature vectors and the ground-truth data in a case where the feature vectors of the same object become close to each other. The function (2) represents the loss Ldist based on the feature vectors and the ground-truth data in a case where the feature vectors of different objects become far away from each other. The function (3) represents the loss Lreg of standardization. The first loss Linst is represented by Equation (4).

$$L_{var} = \frac{1}{C}\sum_{c=1}^{C} \frac{1}{N_c}\sum_{i=1}^{N_c} [|\|\mu_c - x_i\| - \delta_v|]_+^2 \quad (1)$$

$$L_{dist} = \frac{1}{C(C-1)}\sum_{\substack{c_A=1 \\ c_A \neq c_B}}^{C}\sum_{c_B=1}^{C} [2\delta_d - \|\mu_{c_A} - \mu_{c_B}\|]_+^2 \quad (2)$$

$$L_{reg} = \frac{1}{C}\sum_{c=1}^{C}\|\mu_c\| \quad (3)$$

$$L_{inst} = \alpha \cdot L_{var} + \beta \cdot L_{dist} + \gamma \cdot L_{reg} \quad (4)$$

In Equations (1) to (3), C represents the number of labels (that is, objects, in the present embodiment, vertebrae) in ground-truth data 32, Nc represents the number of voxels in each label, xi represents feature vectors, μc represents a vector representing the center of a cluster, $\|\cdot\|$ represents the distance between vectors, and $[\ ]_+$ is an operator representing 0 in a case where the value in [ ] is negative and the value in a case where the value in [ ] is positive. Further, δv represents a margin in the loss Lvar, δd represents a margin in the loss Ldist, and α, β, and γ represent coefficients. For example, coefficients satisfy α=β=1 and γ=0.001.

Figure 5:
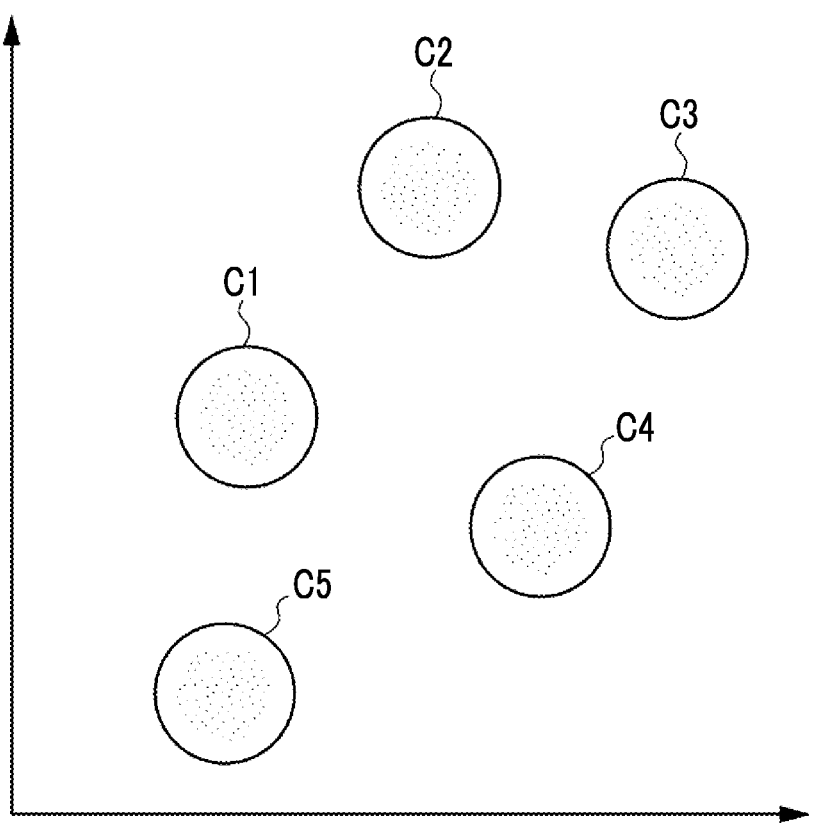
FIG. 5 is a diagram schematically showing the feature map.

As described above, with the learning of the first neural network N1, in a case where the target image is input to the first neural network N1, the feature map in which the feature vectors for the individual objects belonging to the same category included in the target image are clustered and distributed in the feature space is output. FIG. 5 is a diagram schematically showing the feature map. In FIG. 5, the feature map of the two-dimensional feature space is shown assuming that the feature vector is two-dimensional, but the feature map is actually output in the feature space of the dimension corresponding to the dimension of the feature vector. Further, in FIG. 5, the circle represents the cluster, and the points in the cluster represent the feature vectors. In the feature map shown in FIG. 5, the feature vectors of the same object are grouped in five clusters C1 to C5 in the feature space, and the five clusters C1 to C5 are distributed so as to be far away from one another. This means that the target image includes five objects (that is, vertebrae) and the five objects are segmented.

The first learning unit 22 derives the number of convolutional layers constituting the first neural network N1, the kernel coefficient, the kernel size, and the like to perform the learning of the first neural network N1 so that the first loss Linst is a predetermined threshold value or less. As a result, in a case where the target image is input to the first neural network N1, the first neural network N1 outputs the feature map in which the feature vectors for the individual objects (in the present embodiment, vertebrae) belonging to the same category included in the target image are clustered and distributed.

The second neural network N2 is a fully connected neural network having a plurality of processing layers, in which all the nodes included in the processing layer are connected to all the nodes of the adjacent processing layer. A representative value of feature vectors for objects belonging to the same category included in the input image is input to the input layer of the second neural network N2. Here, in the feature map output by the first neural network N1, feature vectors for individual objects belonging to the same category are grouped and distributed as clusters. In the present embodiment, the average value of a plurality of feature vectors included in each cluster in the feature map is used as a representative value of the feature vectors. In a case where the average value is used as the representative value, the representative value is a substantially central value of the cluster in the feature map. At least one of a weighted average value, a median value, a minimum value, or a maximum value may be used as the representative value, instead of the average value. Alternatively, a representative value of all the feature vectors belonging to the same category may be used, instead of the representative value of the feature vectors included in each cluster.

Further, as shown in FIG. 3, the output layer of the second neural network N2 has three nodes, and the probabilities that the clusters of the feature vectors corresponding to the individual objects included in the feature map belong to the cervical vertebrae, the thoracic vertebrae, and the lumbar vertebrae are output as the class classification result from the three nodes, respectively.

In the present embodiment, the second learning unit 23 causes the second neural network N2 to output the class classification result for each cluster of the feature vectors included in the feature map for learning 33 in a case where the feature map for learning 33 and the ground-truth data 32 for the class classification result regarding the plurality of objects belonging to the same category included in the image for learning 31 are input to the second neural network N2. The second learning unit 23 derives a second loss Lcls on the basis of the class classification result. The second loss Lcls is represented by Equation (5). In Equation (5), i represents a cluster, ti represents a target probability for the cluster i, and pi represents a probability representing the class classification result for the cluster i output by the second neural network N2.

$$L_{cls} = \sum_{i}^{C} -t_i \log(p_i) \quad (5)$$

The second learning unit 23 derives a connection weight between the processing layers in the second neural network N2 to perform learning of the second neural network N2 so that the second loss Lcls is a predetermined threshold value or less. That is, the second learning unit 23 performs learning of the second neural network N2 so that the classification result of each cluster for the feature vectors included in the feature map for learning 33 matches the ground-truth data 32. As a result, in a case where the feature map of the target image is input, the second neural network N2 performs output such that the probability of the cervical vertebrae is maximized in a case where the cluster including the feature vectors belongs to the cervical vertebrae, the probability of the thoracic vertebrae is maximized in a case where the cluster belongs to the thoracic vertebrae, and the probability of the lumbar vertebrae is maximized in a case where the cluster belongs to the lumbar vertebrae.

As described above, the first learning unit 22 performs learning of the first neural network N1 and the second learning unit 23 performs learning of the second neural network N2, so that a learned model 40 that outputs the class classification result of the objects of the same category included in the target image in response to the input of the target image is constructed. The learned model 40 is applied to the class classification unit 24.

In a case where the target image is input, the class classification unit 24 causes the learned model 40 to output the class classification result of the vertebrae included in the target image into any class of the cervical vertebrae, the thoracic vertebrae, or the lumbar vertebrae. That is, the class classification unit 24 causes the learned model 40 to output each probability that the individual vertebrae belonging to the same category included in the target image are the cervical vertebrae, the thoracic vertebrae, or the lumbar vertebrae, in a case where the target image is input to the learned model 40. Then, the class classification unit 24 outputs the class having the maximum probability as the class classification result of individual vertebrae included in the target image.

Figure 6:
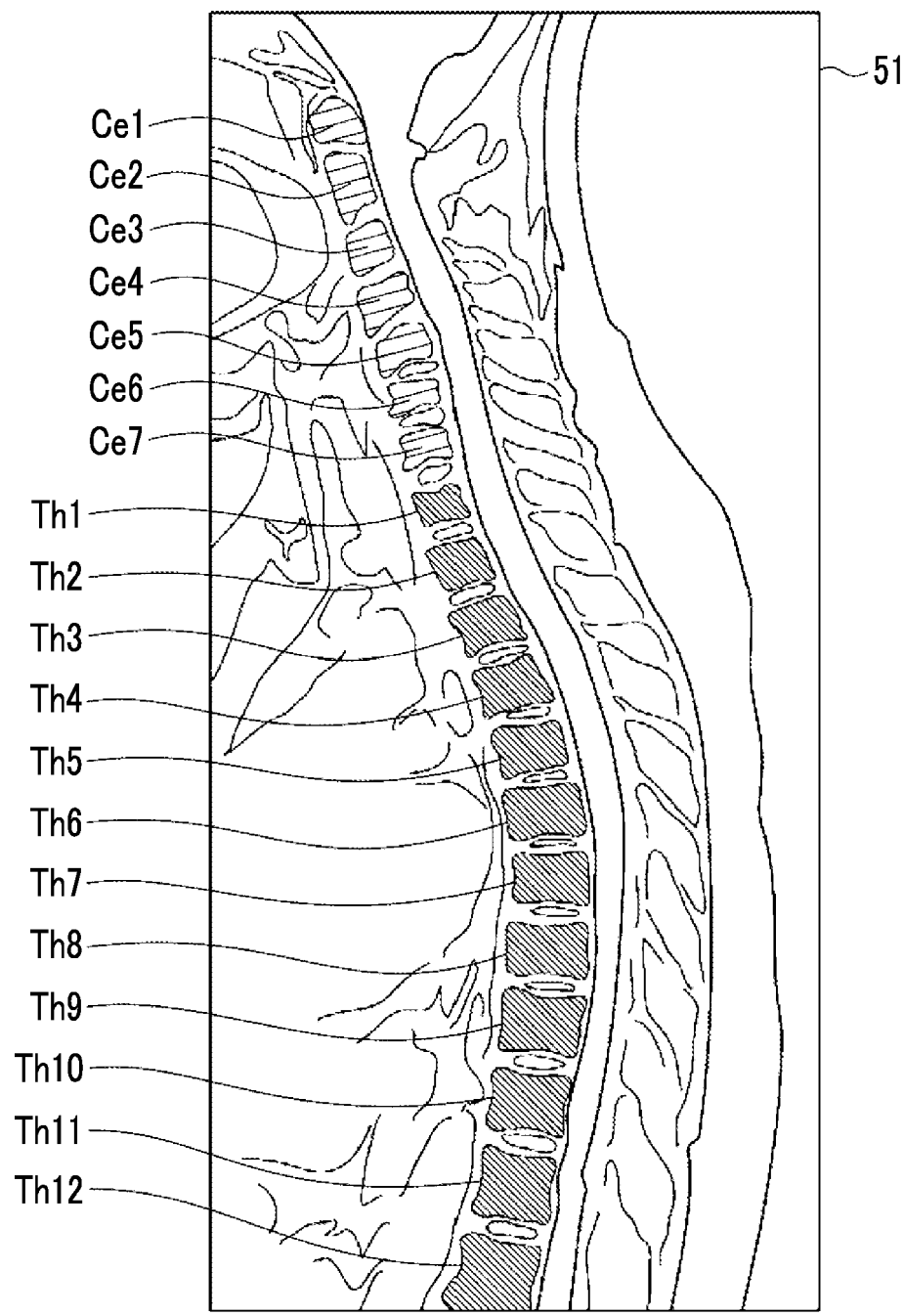
FIG. 6 is a diagram showing a labeled target image.
Figure 7:
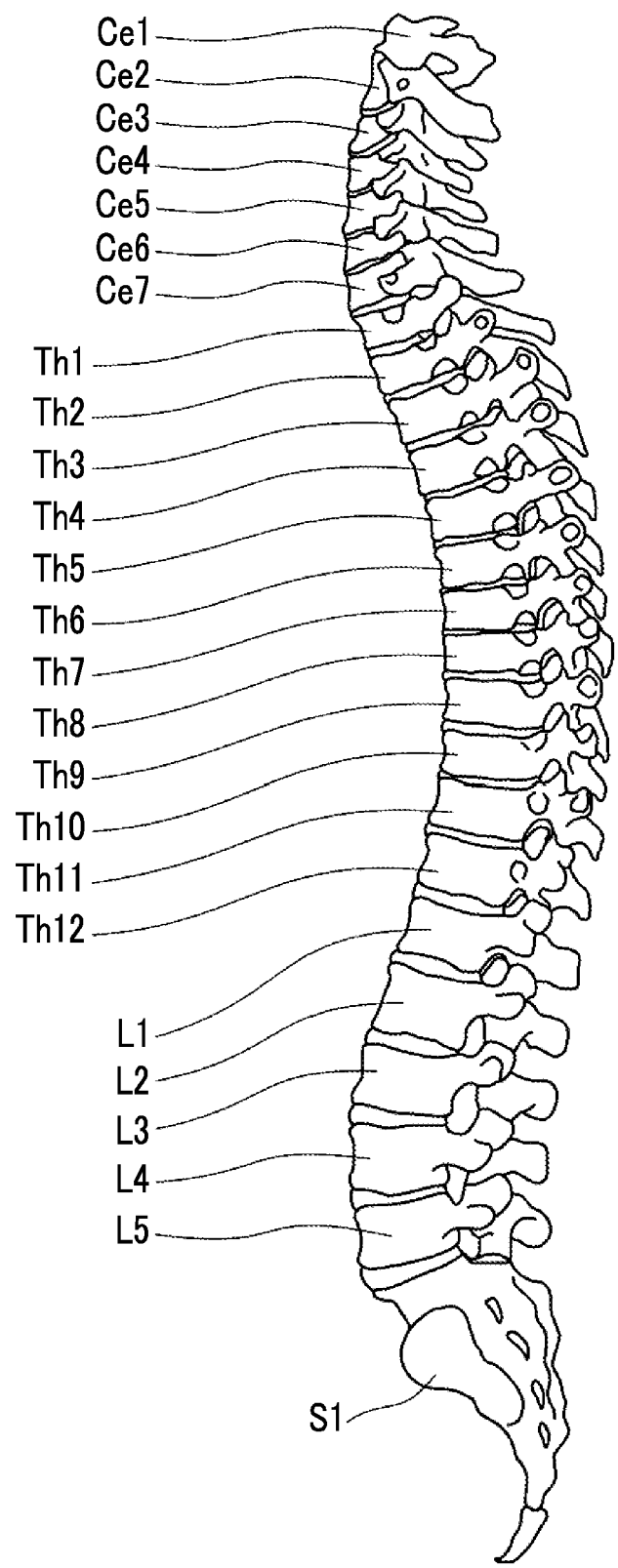
FIG. 7 is a diagram showing labels for cervical vertebrae, thoracic vertebrae, and lumbar vertebrae constituting vertebrae.

The labeling unit 25 labels the vertebrae included in the target image on the basis of the class classification result output by the class classification unit 24. For example, as shown in FIG. 6, in a case where the target image 51 including only the cervical vertebrae and the lumbar vertebrae is input to the class classification unit 24, the class classification unit 24 performs the class classification of the vertebrae included in the target image 51 into the cervical vertebrae Ce's and the thoracic vertebrae Th's. Here, as shown in FIG. 7, the vertebral column consists of seven cervical vertebrae Ce1 to Ce7, twelve thoracic vertebrae Th1 to Th12, and five lumbar vertebrae L1 to L5. In addition, S1 is a sacrum. As described above, the number of vertebrae of each of the cervical vertebrae, the thoracic vertebrae, and the lumbar vertebrae constituting the vertebral column is fixed. Therefore, in a case where the class classification of the vertebrae can be performed into each of the cervical vertebrae, the thoracic vertebrae, and the lumbar vertebrae, individual vertebrae can be labeled. The labeling unit 25 labels the cervical vertebrae and the thoracic vertebrae included in the target image 51 with labels that specify the respective vertebrae. For example, as shown in FIG. 6, the cervical vertebrae hatched with horizontal lines are labeled Ce1 to Ce7 in order from the top, and the thoracic vertebrae hatched with diagonal lines from the upper left to the lower right are labeled Th1 to Th12 in order from the top.

Figure 8:
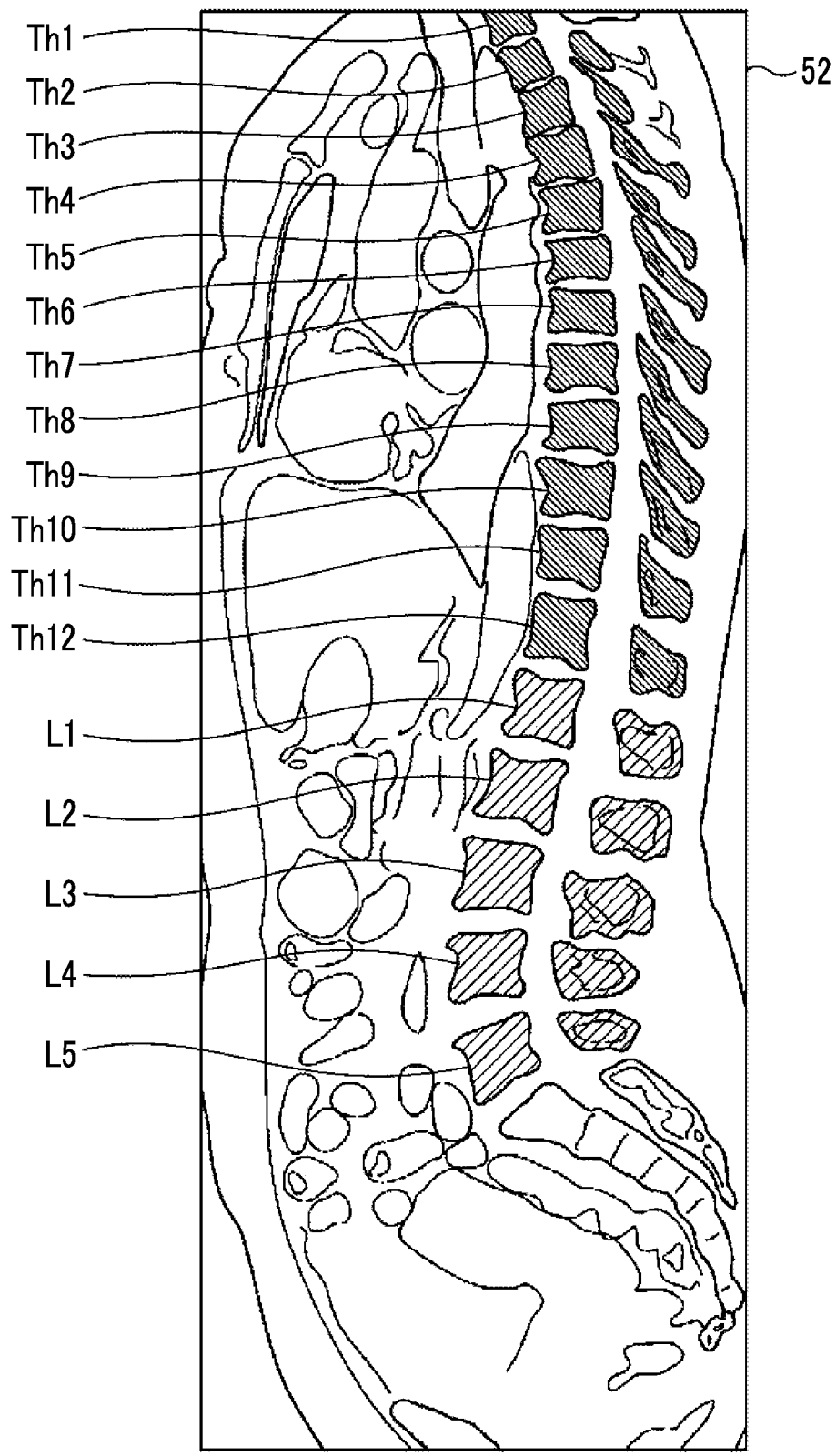
FIG. 8 is a diagram showing another labeled target image.

Further, as shown in FIG. 8, in a case where the target image 52 including only the thoracic vertebrae and the lumbar vertebrae is input, the class classification unit 24 performs class classification of the vertebrae included in the target image 52 into the thoracic vertebrae Th's and the lumbar vertebrae L's. The labeling unit 25 labels the thoracic vertebrae and the lumbar vertebrae included in the target image 52 with different labels from each other. For example, as shown in FIG. 8, the thoracic vertebrae hatched with diagonal lines from the upper left to the lower right are labeled Th1 to Th12 in order from the top, and the lumbar vertebrae hatched with diagonal lines from the upper right to the lower left are labeled L1 to L5 in order from the top.

The display control unit 26 displays the labeled target image on the display unit 14.

Next, processing performed in the present embodiment will be described. FIG. 9 is a flowchart showing learning processing performed in the present embodiment. It is assumed that the image for learning and the ground-truth data are acquired by the image acquisition unit 21 from the image storage server 3 and stored in the storage 13. First, the first learning unit 22 acquires a set of the image for learning and the ground-truth data from a plurality of images for learning and ground-truth data stored in the storage 13 (Step ST1). The first learning unit 22 causes the first neural network N1 to output the feature map for learning 33 in response to the input of the image for learning 31 and the ground-truth data 32, and derives the first loss Linst. Then, the first learning unit 22 perform learning of the first neural network N1 so that the first loss Linst is a predetermined threshold value or less (first learning; Step ST2).

Next, the second learning unit 23 causes the second neural network N2 to output the class classification result of the plurality of vertebrae included in the image for learning 31 in a case where the feature map for learning 33 output by the first neural network N1 is input to the second neural network N2, and derives the second loss Lcls. Then, the second learning unit 23 performs learning of the second neural network N2 so that the second loss Lcls is a predetermined threshold value or less (second learning; Step ST3).

Then, returning to Step ST1, the next image for learning 31 and ground-truth data 32 are acquired from the storage 13, and the processing of Step ST2 and Step ST3 is repeated. As a result, the learned model 40 is constructed.

The first learning unit 22 repeats learning until the first loss Linst becomes a predetermined threshold value or less, but may repeat learning a predetermined number of times. The second learning unit 23 repeats learning until the second loss Lcls becomes a predetermined threshold value or less, but may repeat learning a predetermined number of times.

Next, class classification processing performed in the present embodiment will be described. FIG. 10 is a flowchart of class classification processing performed in the present embodiment. The image acquisition unit 21 acquires the target image (Step ST11), and the class classification unit 24 outputs the class classification result of a plurality of vertebrae included in the target image (Step ST12). Next, the labeling unit 25 labels the vertebrae included in the target image 51 on the basis of the class classification result (Step ST13). Then, the display control unit 26 displays the labeled target image on the display unit 14 (Step ST14), and the processing ends.

As described above, in the present embodiment, in a case where the class classification of the target image is performed, the target image is input to the first neural network N1 included in the learned model 40, so that the feature map is output such that the distance in feature vector between pixels belonging to the same object included in the target image becomes small and the distance in feature vector between pixels belonging to the different objects becomes large. Further, the representative value of the feature vectors for the objects belonging to the same category included in the target image is input to the second neural network N2 included in the learned model 40, so that the class classification result for the plurality of objects belonging to the same category is output. Therefore, according to the present embodiment, the class classification of a plurality of objects belonging to the same category included in the target image can be further performed.

In the above-described embodiment, each of the plurality of vertebrae included in the target image is labeled, but the present disclosure is not limited thereto. Labeling may be performed in order to classify the plurality of vertebrae into three classes of the cervical vertebrae, the thoracic vertebrae, and the lumbar vertebrae.

In addition, in the above-described embodiment, the class classification of the vertebrae included in the target image is performed, but the present disclosure is not limited thereto. The technique of the present disclosure can be applied to a case of class classification of ribs as well as vertebrae. The technique of the present disclosure can also be applied to a case of class classification of a plurality of bones constituting joints such as wrists and ankles. Further, for example, the calf muscle includes not only two types of muscles for bending and stretching, but also a plurality of muscles such as soleus muscle, tibialis anterior muscle, gastrocnemius muscle, and fibula muscle. In this way, the technique of the present disclosure can also be applied to a case of class classification of the plurality of muscles. The image for learning is prepared according to the object as a class classification target, and the learning of the first neural network N1 and the second neural network N2 is performed.

In addition, in the above-described embodiment, the three-dimensional medical image is used as the target image, but the present disclosure is not limited thereto. Individual tomographic images constituting a three-dimensional medical image may be used as the target image. Further, a two-dimensional X-ray image acquired by simple X-ray imaging may be used as the target image. In this case, an image for learning corresponding to the type of the target image is prepared, and the learning of the first neural network N1 and the second neural network N2 is performed.

In addition, in the above-described embodiment, a medical image is used as the target image, but the present disclosure is not limited thereto. For example, a photographic image including a plurality of objects of the same category may be used as the target image.

Further, in the above-described embodiment, for example, as a hardware structure of a processing unit that executes various processing such as processing performed by the image acquisition unit 21, the first learning unit 22, the second learning unit 23, the class classification unit 24, the labeling unit 25, and the display control unit 26, the following various processors may be used. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU which is a general-purpose processor that executes software (programs) to function as various processing units as described above.

One processing unit may be constituted of one of the various processors or may be constituted of a combination of two or more processors of the same type or different types (for example, a combination of a plurality of FPGAs and a combination of a CPU and an FPGA). Further, the plurality of processing units may constitute one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As such, as the hardware structure of various processing units, one or more of the various processors are used.

Furthermore, as the hardware structure of the various processors, more specifically, an electrical circuit (circuitry) in which circuit elements, such as semiconductor elements, are combined may be used.

What is claimed is:

1. A learning apparatus comprising at least one processor, wherein the processor is configured to:
cause a first neural network which extracts a feature vector in each pixel of a target image including a plurality of objects and which outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and that derives a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and
cause a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of the feature vectors for the objects belonging to the same category, and that derives a second loss for the class classification result on the basis of the class classification result for learning and the ground-truth data, to perform learning of the second neural network on the basis of the second loss, wherein the second neural network outputs probabilities that the clusters corresponding to individual objects included in the feature map belong to plurality of classes in response to inputting the feature vector of the target image extracted by the first neural network to the second neural network, wherein the plurality of classes belongs to the same category included in the target image, and
wherein the second neural network outputs the probabilities that the clusters of the feature vectors corresponding to the individual objects included in the feature map belong to the plurality of classes comprising a cervical vertebrae, a thoracic vertebrae, and a lumbar vertebrae are output as the class classification result.

2. The learning apparatus according to claim 1,
wherein the representative value of the feature vectors is a representative value of feature vectors included in a feature vector group that corresponds to each of the individual objects belonging to the same category included in the image for learning.

3. The learning apparatus according to claim 1,
wherein the representative value of the feature vectors is a representative value of feature vectors of all the objects belonging to the same category included in the image for learning.

4. The learning apparatus according to claim 2,
wherein the representative value is at least one of an average value, a weighted average value, a median value, a minimum value, or a maximum value of the feature vectors.

5. The learning apparatus according to claim 1,
wherein the first neural network is a fully convolutional neural network.

6. The learning apparatus according to claim 1,
wherein the second neural network is a fully connected neural network.

7. The learning apparatus according to claim 1,
wherein the target image and the image for learning are three-dimensional medical images.

8. The learning apparatus according to claim 1,
wherein the object is a vertebra, and the class classification result is a classification result of the vertebrae into at least one of cervical vertebrae, thoracic vertebrae, or lumbar vertebrae.

9. A class classification apparatus comprising:
a class classification unit to which a learned model including the first neural network and the second neural network of which learning is performed by the learning apparatus according to claim 1 is applied, and which outputs a class classification result of a plurality of objects belonging to the same category included in the target image in response to input of the target image.

10. The class classification apparatus according to claim 9, wherein the processor is further configured to:
label the objects included in the target image according to the class classification result; and
display the labeled target image on a display.

11. A learned model comprising:
the first neural network and the second neural network of which learning is performed by the learning apparatus according to claim 1.

12. A learning method comprising:
causing a first neural network which extracts a feature vector in each pixel of a target image including a plurality of objects and outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and deriving a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and
causing a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of feature vectors for the objects belonging to the same category, and deriving a second loss for the class classification result on the basis of the class classification result for learning and the ground-truth data, to perform learning of the second neural network on the basis of the second loss,
wherein the second neural network outputs probabilities that the clusters corresponding to individual objects included in the feature map belong to plurality of classes in response to inputting the feature vector of the target image extracted by the first neural network to the second neural network, wherein the plurality of classes belongs to the same category included in the target image, and
wherein the second neural network outputs the probabilities that the clusters of the feature vectors corresponding to the individual objects included in the feature map belong to the plurality of classes comprising a cervical vertebrae, a thoracic vertebrae, and a lumbar vertebrae are output as the class classification result.

13. A class classification method comprising:
outputting a class classification result of a plurality of objects belonging to the same category included in the target image in response to input of the target image, by using a learned model including the first neural network and the second neural network of which learning is performed by the learning method according to claim 12.

14. A non-transitory computer-readable storage medium that stores a learning program causing a computer to execute a process comprising:
causing a first neural network which extracts a feature vector in each pixel of a target image including a plurality of objects and outputs a feature map in which feature vectors of pixels belonging to individual objects included in the target image are clustered and distributed as a plurality of feature vector groups in a feature space which is a space of the feature vector, to output a feature map for learning for an image for learning in response to input of the image for learning and ground-truth data for a class classification result regarding a plurality of objects belonging to the same category included in the image for learning, and deriving a first loss between pixels in the image for learning as a function in which a distance in feature vector between pixels belonging to the same object in the image for learning becomes small and a distance in feature vector between pixels belonging to different objects becomes large, on the basis of distribution of a plurality of feature vector groups in the feature map for learning and the ground-truth data, to perform learning of the first neural network on the basis of the first loss; and
causing a second neural network which outputs a class classification result of a plurality of objects belonging to the same category included in the target image in response to input of the feature vector of the target image, to output a class classification result for learning for the plurality of objects belonging to the same category included in the image for learning in response to input of a representative value of feature vectors for the objects belonging to the same category, and deriving a second loss for the class classification result on the basis of the class classification result for learning and the ground-truth data, to perform learning of the second neural network on the basis of the second loss,
wherein the second neural network outputs probabilities that the clusters corresponding to individual objects included in the feature map belong to plurality of classes in response to inputting the feature vector of the target image extracted by the first neural network to the second neural network, wherein the plurality of classes belongs to the same category included in the target image, and
wherein the second neural network outputs the probabilities that the clusters of the feature vectors corresponding to the individual objects included in the feature map belong to the plurality of classes comprising a cervical vertebrae, a thoracic vertebrae, and a lumbar vertebrae are output as the class classification result.

15. A non-transitory computer-readable storage medium that stores a class classification program causing a computer to execute a process comprising:

outputting a class classification result of a plurality of objects belonging to the same category included in the target image in response to input of the target image, by using a learned model including the first neural network and the second neural network of which learning is performed by the learning method according to claim 12.

* * * * *